United States Patent
Tanaka et al.

(10) Patent No.: US 11,219,590 B2
(45) Date of Patent: Jan. 11, 2022

(54) ANTI-AGING AGENT AND ANTI-AGING METHOD

(71) Applicants: Megumi Tanaka, Kanagawa (JP); Tsunemaru Tanaka, Tanaka (JP)

(72) Inventors: Megumi Tanaka, Kanagawa (JP); Tsunemaru Tanaka, Tanaka (JP)

( * ) Notice: Subject to any disclaimer, the term of this patent is extended or adjusted under 35 U.S.C. 154(b) by 0 days.

(21) Appl. No.: 16/646,578

(22) PCT Filed: Sep. 14, 2018

(86) PCT No.: PCT/JP2018/034195
§ 371 (c)(1),
(2) Date: Mar. 12, 2020

(87) PCT Pub. No.: WO2019/054485
PCT Pub. Date: Mar. 21, 2019

(65) Prior Publication Data
US 2020/0268632 A1   Aug. 27, 2020

(30) Foreign Application Priority Data
Sep. 14, 2017   (JP) .............................. JP2017-176382

(51) Int. Cl.
| | |
|---|---|
| *A61K 8/60* | (2006.01) |
| *A61K 31/706* | (2006.01) |
| *A61K 9/00* | (2006.01) |
| *A61Q 19/00* | (2006.01) |
| *A61Q 19/08* | (2006.01) |

(52) U.S. Cl.
CPC ............ *A61K 8/606* (2013.01); *A61K 9/0056* (2013.01); *A61K 31/706* (2013.01); *A61Q 19/007* (2013.01); *A61Q 19/08* (2013.01)

(58) Field of Classification Search
CPC .... A61K 8/606; A61K 31/706; A61K 9/0056; A61Q 19/08; A61Q 19/007
USPC ......................................................... 514/52
See application file for complete search history.

(56) References Cited

U.S. PATENT DOCUMENTS 10,898,738 B2 *  1/2021  Tanaka ................ A61K 9/0048
2017/0165282 A1   6/2017  Rongzhao et al.

FOREIGN PATENT DOCUMENTS

| CN | 106 617 026 A | | 5/2017 |
|---|---|---|---|
| WO | WO 2014/146044 | * | 9/2014 |
| WO | 2016/210232 A1 | | 12/2016 |
| WO | 2017/110317 A1 | | 6/2017 |

OTHER PUBLICATIONS

ISR; European Patent Office; Munich; Jan. 26, 2021.
Add To Basket Submit Drugstore & Body Care Baby Care Erotic Household Contact Lenses Nutrition Shaving & Hair Removal Health Supply Store All Amazonbasics Best Sellers Prime Video New Releases Today's Deals Hello; Sep. 24, 2016.
Database GNPD; "Skin Cream"; Dec. 28, 2016.
Natalie E. De Picciotto et al Nicotinamide Mononucleoride Supplementation Reverses Vascular Dysfunction and Oxidative Stress With Aging in Mice; Mar. 11, 2016.
Mills Kathryn F et al: "Long-Term Administration of Nicotinamide Mononucleotide Mitigates Age Associated Physiological Decline in Mice"; Oct. 27, 2016.
Al Greenbaum et al; "The Effect If Different Hormonal Conditions On the Concentration and Oxidoreduction State of the Nicotinamide Nucleotides of Rat Liver"; Apr. 1, 1965.
Grabowska Wioleta et al; "Sirtuins, A Promising Target in Slowing Down the Ageing Process"; Mar. 3, 2017.

* cited by examiner

*Primary Examiner* — Yih-Horng Shiao
(74) *Attorney, Agent, or Firm* — Patshegen IP LLC; Moshe Pinchas

(57) ABSTRACT

PROBLEM: To provide an anti-aging agent and a method for the anti-aging that are safe in long-term intake and ensures effective suppression of the progress of the aging.
SOLUTION: Nicotinamide mononucleotide is contained as an active ingredient.

3 Claims, 4 Drawing Sheets

ANTI-AGING AGENT AND ANTI-AGING METHOD

TECHNICAL FIELD

The present invention relates to an anti-aging agent and a method for anti-aging.

BACKGROUND ART

A human lifespan has been steadily increasing due to, for example, development of medical science and improvement of public health. According to a recent report, it is expected that, in japan, an average lifespan of male will be 84.19 years and that of female 90.93 years, which exceeds 90 years, in 2060. It is reported that a percentage of the population aged 65 and over in the total population (an aging rate) in japan is about 25% and an aging society is rapidly in progress. It is expected that the aging rate will continue to rise in accordance with a rise of the average lifespan, and the aging society will further continue.

Meanwhile, as one of problems that the aging society in japan is facing, it is pointed out that the rise in a healthy lifespan imposing no restricted daily life is smaller compared to the rise of the average lifespan and the difference between the average lifespan and the healthy lifespan is widening. While the aging is a phenomenon that any living being cannot avoid, everyone desires to delay the aging even a little and extend the healthy lifespan so as to live long in good health.

In order to solve such a problem in the aging society, recently, research in a field of anti-aging medicine that considers the aging as one disease and tries to delay the onset itself of the aging by treatment has been actively conducted. The anti-aging medicine covers wider areas, for example, internal secretion, metabolism, arteriosclerosis, nourishment, locomotorium, and sense organs, subjects not only the elderly people but also all ages, and aims to extend one's healthy time with a more youthful physical function than that of one's current age.

Generally, the aging is understood to be the phenomenon where the number of cells decreases with the aging, and physical, physiological, and mental functions decline. A physical change due to the aging begins at about 40 years old after reaching a maturity stage, showing, for example, skin wrinkles, a loss of scalp hair and teeth, a deterioration of eyesight and hearing, a decline of motor function, and a decrease of bone mass. While the aging is not a disease in itself, the decline of physical and physiological functions increases a risk of so-called geriatric diseases such as arteriosclerosis, osteoporosis, and cataract, and causes the aging of the mental functions such as memory and learning accompanied with the decline of the physical function.

In the field of the anti-aging medicine, research on the aging has been advanced in many areas; as a result, several hypotheses for the causes of the aging have been proposed, as shown below. However, all of these are still hypothetical levels, and are not fully elucidated at present.

1) Gene Program Theory

A portion referred to as telomere is located at an end of a chromosome that carries gene information, works to correctly copy and pass the gene information during a cell division, gets shorter with each cell division; it is considered that shortening of the telomere to some extent causes a telomere dysfunction, which causes decreased regeneration of cells to decline the organizational functions. That is, the number of times of the cell division is limited by telomere; when the cell division becomes impossible, an activity of the living body is inevitably lost, leading to the aging.

2) DNA Damage Theory

It is considered that when DNA is damaged by stimulation such as ultraviolet rays and an atmospheric pollutant and the cell division occurs before the damage is repaired, an accumulation of the damaged and deteriorated information results in the aging. While the damaged DNA is constantly repaired, a repair rate decreases by increasing the age.

3) Active Oxygen Theory

It is considered that when a part of the oxygen that is not used inside the living body becomes active oxygen and oxidizes the cells, the oxidized cells cannot work normally, resulting in progress of the aging. It is pointed out that reasons for easily generating the active oxygen include, for example, exposure to ultraviolet rays, stresses, smoking and an atmospheric contamination environment, a diet rich in fats and eating habits with many additives.

4) Hormone Theory

It is considered that, in proportion to age, the secretion of specific hormones, for example, "a growth hormone" related to metabolic control, "melatonin" related to sleep, "a sex hormone" related to reproduction of the respective males and females reduces, resulting in the loss of a physiological function with those hormones and the progress of the aging.

5) Immune Function Theory

It is considered that, with the aging, a decline of immune function against foreign pathogens and the onset of excessive inflammatory reaction tendency cause the decline of metabolism and cell regeneration, accelerating the aging. For the reason of the decline of the immune function with the aging, the relationship with thymus atrophy is pointed out. The thymus is a central organ for differentiation and growth of T-cells and an immune response manifestation and is known to atrophy with the aging.

According to previous studies, improving a daily lifestyle, having balanced eating habits, and doing moderate exercises are important for suppressing the progress of the aging and keeping youthful healthy condition. Of these, with regard to eating habits, in recent years, food ingredients effective in suppressing the aging have come to be generally known; for example, as the food ingredients that suppress the aging of the brain, docosahexaenoic acid (DHA), eicosapentaenoic acid (EPA), a vitamin B group ($B_6$, $B_{12}$, folic acid), lecithin, choline, and tryptophan are known; as the food ingredients that enhance immunity, vitamin A, vitamin E, vitamin C, the vitamin B group (pantothenic acid, $B_6$, $B_{12}$, folic acid), and zinc are known; as the food ingredients that increase bone mass, calcium, protein, vitamin D, and vitamin K are known; as the food ingredients that remove active oxygen, a carotenoid (lycopene, lutein, vitamin A, and the like), astaxanthin, polyphenols (flavonoid, catechin, isoflavone, sesamin, curcumin, and the like), vitamin E, vitamin C, coenzyme Q, and the like are known. On the other hand, as enzymes that eliminate the active oxygen, superoxide dismutase (SOD), glutathione peroxidase, catalase, and the like are known.

Recently, new anti-aging agents for suppressing the aging have been developed. For example, as the anti-aging agent that can suppress skin aging, particularly can improve pigmentation of the skin, the anti-aging agent that includes at least one type selected from a group consisting of (A) ascorbic acid 2-glucoside and its salt, and at least one type selected from a group consisting of (B) adenine, adenosine, adenosine 2'-monophosphate, adenosine 3'-monophosphate, adenosine 5'-monophosphate, cyclic adenosine 3', 5'-monophosphate, adenosine 5'-diphosphate, and adenosine 5'-triphosphate, and salts of these are reported (Patent Document 1).

As other examples, the anti-aging agent characterized in compounding an extracted material obtained by an enzyme treatment using cellulase in an extraction process of extracting *Sargassum horneri* of the genus *Sargassum* of brown algae with water as an active ingredient is reported (Patent Document 2).

Patent Document 1: JP-4129574
Patent Document 2: JP-4926448

DISCLOSURE OF THE INVENTION

Problems to be Solved by the Invention

It is an object of the present invention to provide an anti-aging agent and a method for anti-aging that reduces progress of the aging and is effective in recovering youthfulness and is safe in long-term intake.

Solutions to the Problems

The inventor seriously studied in order to solve the above-described problems and found that a nicotinamide mononucleotide as an intermediate metabolite involved in biosynthesis of a coenzyme NAD (nicotinamide adenine dinucleotide) has an excellent anti-aging effect. Thus, the present invention was completed.

The present invention is as follows.
[1] An anti-aging agent that contains a nicotinamide mononucleotide as an active ingredient.
[2] The anti-aging agent according to [1] where the anti-aging agent is used for improving an aging symptom of skin, a dry skin, skin blemishes, freckles, or a rough skin.
[3] The anti-aging agent according to [1] where the anti-aging agent is used for improving hormone secretion.
[4] The anti-aging agent according to [3] where the hormone is one type, or two or more types selected from a growth hormone, a thyroid gland hormone, an adrenocortical hormone, a sex hormone, prolactin, an antidiuretic hormone, a parathyroid hormone, and melatonin.
[5] The anti-aging agent according to [1] where the anti-aging agent is used for reducing active oxygen inside a living body.
[6] The anti-aging agent according to any of [1] to [5] where the anti-aging agent is a food product for anti-aging.
[7] The anti-aging agent according to any of [1] to [5] where the anti-aging agent is a medical product for anti-aging.
[8] A method for anti-aging that includes causing a subject to ingest an effective dose of a nicotinamide mononucleotide, the subject needing the effective dose of the nicotinamide mononucleotide (excluding a medical treatment for human).

Effects of the Invention

The present invention has an excellent anti-aging effect. The present invention ensures the effective improvement of the visual function. The present invention is safe because the nicotinamide mononucleotide as the intermediate metabolite involved in the biosynthesis of in vivo $NAD^+$ is contained as the active ingredient. The present invention ensures the long-term intake.

DESCRIPTION OF PREFERRED EMBODIMENTS

An anti-aging agent according to the present invention contains a nicotinamide mononucleotide as an active ingredient and provides anti-aging effect. In the present invention, "anti-aging" has a broader meaning including, for example, an improvement of aging phenomena, a delay of aging, and rejuvenation, in addition to the anti-aging in a narrow sense, including everything such as suppression, an improvement, a delay, rejuvenation, normalization of a decline of a physical function, a physiological function, and a mental function with the aging. Specifically, "anti-aging" means effects such as the suppression, the improvement, and the delay against, for example, skin aging symptoms (wrinkles, an occurrence of sagging, a loss of skin tension, and the like), a dry skin with the aging (deterioration of a moisture-retaining property of the skin), skin blemishes, freckles, a rough skin, decrease and increase of hormone (a growth hormone, a thyroid gland hormone, an adrenocortical hormone, a sex hormone, prolactin, an antidiuretic hormone, a parathyroid hormone, melatonin, and the like) secretion, damage of cells (brain cells, myocardial cells, and the like) by active oxygen, a loss of scalp hair and teeth, deterioration of eyesight and hearing, deterioration of a motor function, decrease of a bone mass, decrease of physical strength, a decline in a memory, a decline of a learning ability, a decline of an immune function, and an occurrence of a geriatric disease.

The detailed reason why containing the nicotinamide mononucleotide as the active ingredient provides such an effect is currently examined. However, it is conceivable to be one of the main reasons that the nicotinamide mononucleotide promotes a "sirtuin" typified by $NAD^+$ dependent deacetylases Sirt1 and Sirt3, and consequently, normalizes the hormone secretion system such as glucose tolerance, the growth hormone, and cortisol. The following describes the present invention in detail.

The nicotinamide mononucleotide (chemical formula: $C_{11}H_{15}N_2O_8P$) is a compound produced in bodies of many organisms including human, and expressed with a structural formula [Chem. 1] below. The nicotinamide mononucleotide is generally referred to as NMN, and known as an intermediate metabolite involved in a biosynthesis of coenzyme NAD+.

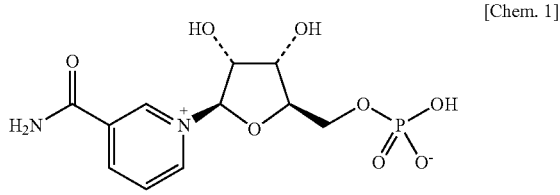

[Chem. 1]

Figure 1:
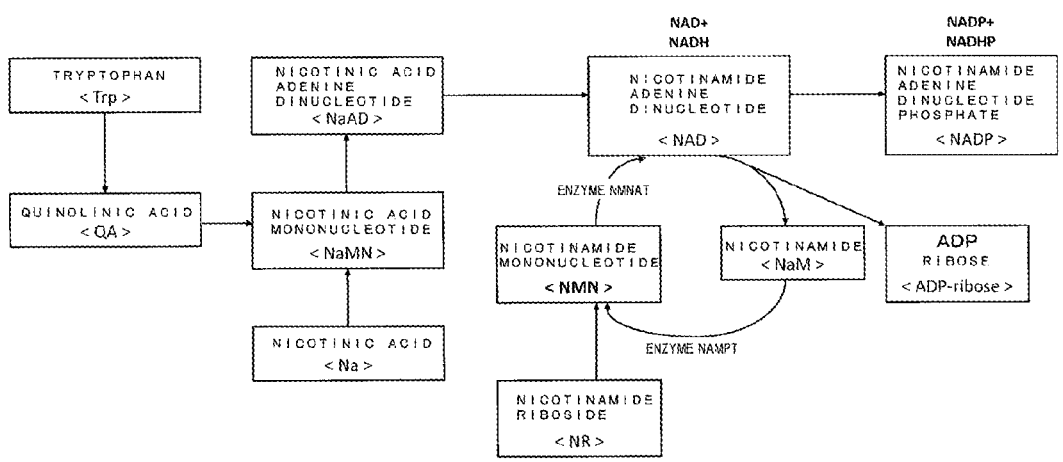
FIG. 1 is an explanatory drawing illustrating a metabolic pathway involved in niacin (generic term of nicotinamide and nicotinic acid).

The nicotinamide mononucleotide as the active ingredient of the anti-aging agent is produced in an NAD metabolic pathway by liver tissues, that is, a pathway involved in a synthesis of a nicotinamide adenine dinucleotide (NAD) from a quinolinic acid through a kynurenine pathway, in vivo. This will be specifically described with reference to FIG. 1. FIG. 1 is an explanatory drawing illustrating a metabolic pathway involved in niacin (generic term of a nicotinamide and a nicotinic acid) known as vitamin $B_3$. The nicotinic acid ingested through a meal is absorbed by the liver to be converted into nicotinamide, and the nicotinamide is supplied to the whole body via a blood flow. The cells each absorb the nicotinamide from the blood, and convert it into the NAD and an NADP to use them. The nicotinamide is biosynthesized also from a tryptophan.

As illustrated in FIG. 1, in vivo, when the tryptophan is a starting material, the tryptophan is converted into the quinolinic acid (QA) through the kynurenine pathway as a tryptophan metabolic pathway, and further converted into a nicotinic acid mononucleotide (NaMN). Meanwhile, when the nicotinic acid (Na) is the starting material, the nicotinic acid is directly converted into the NaMN. Afterwards, the NaMN is interconverted into the NAD, a nicotinamide (NaM), and the nicotinamide mononucleotide in a NAD cycle through a nicotinic acid adenine dinucleotide (NaAD). The nicotinamide (NaM) is converted into the nicotinamide mononucleotide by a nicotinamide phosphoribosyltransferase (NAMPT), subsequently, the nicotinamide mononucleotide is converted by a nicotinamide mononucleotide adenyltransferase (NMNAT) to generate the NAD. Note that, the nicotinamide mononucleotide is produced also from a nicotinamide riboside (NR) as an NAD intermediate metabolite.

The nicotinamide mononucleotide includes two types of an α-form and a β-form as optical isomers, and the β-form is used in the present invention. The nicotinamide mononucleotide is obtained by, for example, synthesizing a nicotinamide riboside from the nicotinamide and a ribose (see Bioorg. Med. Chem. Lett., 12, 1135-1137 (2002)), and subsequently, phosphorylating a 5-hydroxyl group of the ribose part (see Chem. Comm., 1999, 729-730). Specifically, for example, first, a reaction solution is prepared by dissolving the nicotinamide and an L-ribose tetraacetate in anhydrous acetonitrile, adding a trimethylsilyl trifluorosulfonic acid by an excessive amount under a nitrogen stream and then stirring at room temperature, and adding methanol to stop the reaction. The above-described reaction solution is poured into a column filled with activated carbon, cleaned with a distilled water, and then eluted with methanol and its product is collected. Next, for a phosphorylation reaction of the 5-hydroxyl group of the L-ribose part of this product, a reaction solution is prepared by dissolving the above-described product in a trimethoxy phosphoric acid, dropping a phosphorus oxychloride below freezing and stirring under the nitrogen stream, adding a sodium hydroxide aqueous solution to neutralize, thus stopping the reaction. A cold acetonitrile-ether solution is added to the above-described reaction solution. Afterwards, a lower layer (water phase) is passed through an anion-exchange resin to collect a reactant, and further purifies the reactant with a cation-exchange resin, thus the high-purity nicotinamide mononucleotide can be collected. The nicotinamide mononucleotide is commercially available from Oriental Yeast Co., ltd. and Bontac Bio-engineering (Shenzhen) Co., Ltd., and those commercial products can be purchased for use.

The nicotinamide mononucleotide is a purified product that contains a few impurities, especially, preferably its purity is 90% or more, and further preferably its purity is 95% or more. When the purity is 90% or less, a bad smell possibly occurs, or the effect of the nicotinamide mononucleotide is possibly reduced to fail to sufficiently provide the effect of the present invention.

While the purity of the nicotinamide mononucleotide is preferably 90% or more as described above, the purity (mass ratio) is defined as a value obtained by subtracting the impurities other than the nicotinamide mononucleotide from 100% in anhydrous terms. Accordingly, the purity of the nicotinamide mononucleotide can be obtained with a formula: nicotinamide mononucleotide purity (%)=100−impurities other than nicotinamide mononucleotide (%). Here, these impurities include, as illustrated in FIG. 1, metabolites excluding the nicotinamide mononucleotide involved in the NAD metabolic pathway, especially, the nicotinamide and the nicotinamide adenine dinucleotide. When the nicotinamide mononucleotide used in the present invention contains a foreign element such as the above-described metabolite involved in the NAD metabolic pathway, for example, the absorption of the nicotinamide mononucleotide into living cells possibly reduces, resulting in the reduction of the effect of the present invention. A quantitative determination of the above-described impurities involved in the NAD metabolic pathway is performed with an absolute calibration curve method using a standard sample where a test solution of dried nicotinamide mononucleotide powder is poured into an HPLC apparatus, and a peak area of an obtained chromatograph is obtained (vertical axis: peak area, horizontal axis: concentration). Since the use of the peak height ensures the quantitative determination with high accuracy in a case of a trace substance, the apparatus to be used is appropriately chosen according to the characteristics of the apparatus. Separated substances are identified based on retention times.

The anti-aging agent according to the present invention is easily manufactured by using the nicotinamide mononucleotide alone or mixing another ingredient. The other ingredient is not specifically limited insofar as the effect of the present invention is provided.

The example of other ingredients include, as described above, docosahexaenoic acid (DHA), eicosapentaenoic acid (EPA), a vitamin B group ($B_6$, $B_{12}$, folic acid), lecithin, choline, and tryptophan known as food ingredients that suppress brain aging; vitamin A, vitamin E, vitamin C, the vitamin B group (pantothenic acid, $B_6$, $B_{12}$, folic acid), and zinc known as the food ingredients that enhance immunity; calcium, a protein, vitamin D, and vitamin K known as the food ingredients that increase the bone mass; carotenoid (lycopene, lutein, vitamin A, and the like), astaxanthin, polyphenols (flavonoid, catechin, isoflavone, sesamin, curcumin, and the like), vitamin E, vitamin C, coenzyme Q, and the like known as the food ingredients that remove the active oxygen. Auxiliary ingredients commonly used in a food sector, for example, various vitamins, a trace element, a citric acid, a malic acid, a fragrance, and inorganic salts may be included as the other ingredients.

In the present invention, the other ingredient especially effective in increasing the anti-aging effect includes resveratrol. The resveratrol is known as an antioxidant substance contained in, for example, a grape peel, red wine, a peanut peel, a Japanese knotweed, and a gnetum gnemon. The resveratrol includes trans and cis isomers, a trans/cis isomer mixture, a dimer, and a resveratrol derivative such as methylated resveratrol. The trans isomer stable against heat is usually used for the health food and the like. The resveratrol may be synthetically prepared in addition to one prepared by being extracted from every raw material and purified.

A compounding ratio of the resveratrol and the nicotinamide mononucleotide is not limited. However, from an aspect of extracting the maximum effect of the present invention, the compounding ratio of both is preferably adjusted such that in a daily intake per adult, the resveratrol is 1 to 100 pts.mass while the nicotinamide mononucleotide is 1 to 25 pts.mass.

The anti-aging agent according to the present invention is mainly taken orally to suppress the aging. In the present invention, as described before, "anti-aging" has a broader meaning including, for example, the improvement of the aging phenomena, the delay of the aging, and the rejuvenation, in addition to anti-aging in a narrow sense, thus including everything such as the suppression, the improvement, the delay, the rejuvenation, the normalization of the decline of the physical function, the physiological function, and the mental function with the aging. Specifically, "anti-aging" may include the effects of the suppression, the improvement, and the delay against, for example, the occurrence of the skin aging symptoms (wrinkles, the occurrence of the sagging, the loss of the skin tension, and the like), the dry skin with the aging (the deterioration of the moisture-retaining property of the skin), the skin blemishes, the freckles, the occurrence of the rough skin, the decrease and increase of hormone (the growth hormone, the thyroid gland hormone, the adrenocortical hormone, the sex hormone, prolactin, the antidiuretic hormone, the parathyroid hormone, melatonin, and the like) secretion, the damage of the cells (the brain cells, the myocardial cells, and the like) by the active oxygen, the loss of the scalp hair and the teeth, the deterioration of the eyesight and the hearing, the deterioration of the motor function, the decrease of the bone mass, the decrease of the physical strength, the decline in the memory, the decline of the learning ability, the decline of the immune function, and the occurrence of the geriatric disease.

The anti-aging agent according to the present invention is effective to the skin aging symptoms, the dry skin with the aging (deterioration of the moisture-retaining property of the skin), the skin blemishes, the freckles, and the rough skin. Here, "the skin aging symptom" mainly means, for example, the wrinkles, the occurrence of the sagging, and the loss of the skin tension due to deterioration of elasticity in the skin with the aging. For the reason why the present invention suppresses and improves the skin aging symptom, it is conceivable that the nicotinamide mononucleotide activates a weakened skin metabolic function, promotes collagen formation, and, in addition, as will be described later, decreases the active oxygen.

The anti-aging agent according to the present invention can be used to improve the dry skin by providing the skin of a face, hands, and the like with moisture, and continuously improving the moisture-retaining property of the skin. Application of the present invention increases the skin moisture amount and improve the moisture-retaining property of the skin, resulting in the improvement of, for example, dryness, the tension, the elasticity, and flexibility of the skin. For the reason why the present invention improves the skin moisture-retaining property, it is conceivable, for example, that the nicotinamide mononucleotide influences of a natural moisturizing factor and horny intercellular lipid and promotes hyaluronan formation.

The anti-aging agent according to the present invention can be used to obtain a whitening effect that suppresses formation and deposition of melanin with the aging and suppresses or improves the skin blemishes and the freckles. For the reason why the present invention provides the whitening effect, it is conceivable, for example, that the nicotinamide mononucleotide promotes a discharge of the melanin.

The anti-aging agent according to the present invention can be used to suppress and improve the rough skin with the aging. Corresponding to the cause of the rough skin, it is more effective to appropriately combine, for example, an anti-inflammatory agent, the vitamins, the hormone, a plant extract, bactericide, and an oily ingredient. For the reason why the present invention exerts the suppression and improvement effects for the rough skin, it is conceivable, for example, that the nicotinamide mononucleotide improves the activity of sirtuin in skin tissue.

Additionally, the anti-aging agent according to the present invention improves one type, or two or more types of the secretion selected from the several hormones (the hormone the secretion quantity of which reduces mainly in proportion to age), specifically, for example, the growth hormone, the thyroid gland hormone, the adrenocortical hormone, the sex hormone, prolactin, the antidiuretic hormone, the parathyroid hormone, and the melatonin, rejuvenates the physiological effect provided by each of these hormones, thus exerting the anti-aging effect. Therefore, the anti-aging agent according to the present invention can be used as an application for improving the secretion of these hormones. In addition, "the improvement of the hormone secretion" means to promote or reduce the hormone secretion quantity to direct the hormone secretion quantity in an appropriate direction.

The growth hormone is a hormone that is mainly secreted around a pituitary gland in a hypothalamus. The growth hormone is secreted into a subject organ to promote the growth of that organ tissue, and acts to control metabolism. The growth hormone, also referred to as "a rejuvenation hormone", has a decline in basal secretion and reactivity with the aging. It is considered that mechanisms of this decline include, for example, decrease of somatotroph cells, decrease of the production quantity, a decline of reactivity to a growth hormone-releasing hormone, increase of sensitivity to an insulin-like growth factor (IGF-1) of the somatotroph cells, growth hormone-releasing hormone hyposecretion in the hypothalamus, and supersecretion of somatostatin. In the case of adults, the growth hormone is said to play an important role in maintaining a normal feeling of well-being of healthy people. In addition, the growth hormone is said to exert the effects of, for example, enhancement in memory, suppression of a feeling of fatigue and a decline in a mood, acceleration of a bone density, retention of a reproductive function, enhancement of the immune function, acceleration of fat combustion, and promotion of muscle growth.

The thyroid gland hormone is a hormone secreted from the thyroid gland, where two types of thyroxin ($T_4$) and triiodothyronine ($T_3$) are known, generally acts on the cells throughout the body to increase a cell metabolic rate. It is known that a function of the thyroid gland itself deteriorates with the aging and the reactivity of a thyroid-stimulating hormone (TSH) against a thyroid-hormone-releasing hormone (TRH) deteriorates to decrease the secretion quantity of triiodothyronine. Specifically, the thyroid gland hormone is said to exert the effects, for example, the enhancement of the skin moisture-retaining property, the enhancement in the memory, the suppression of the fatigue and the decline in the mood, suppression of a middle-aged spread, suppression of being sensitive to cold, and suppression of thinning hair.

The adrenocortical hormone is a hormone secreted from an adrenal cortex. The adrenal cortex is divided into a glomerular, a fascicular, and reticular zones. The glomerular zone produces a mineral corticoid, the fascicular zone produces a glucocorticoid, and the reticular zone produces an adrenal androgen. The adrenocortical hormone has many physiological effects, for example, an anti-inflammatory effect, an immunosuppressive effect, an antistress effect, a water-electrolyte regulatory effect, a carbohydrate metabolism effect, a lipid metabolism effect, an anabolic effect, an anabolic suppression effect, a blood coagulation acceleration effect, and a pituitary suppression effect. In addition, the androgen is a generic term for male hormones. A biological activity as the male hormone of the adrenal androgen is weaker compared to testosterone secreted from testicles.

The sex hormones are broadly classified into the male hormone that is mainly produced in a testicular interstitial cell and the female hormone that is secreted from an ovary. The male hormone serves to enhance so-called male characteristics, which peaks at the age of 20 to 30, and the secretion gradually decreases thereafter. The typical male hormone is the testosterone. The male hormones have the functions of, for example, maintaining bone and muscle strength, maintaining a sexual function, maintaining vascular conditions, suppressing arteriosclerosis, and suppressing a metabolic syndrome. On the other hand, there are two types of the female hormones: a follicle hormone (estrogen), which creates femininity, and a corpus luteum hormone (progesterone), which helps pregnancy. The female enters the menopause around the age of 50; the secretion of the female hormones is drastically reduced, and osteoporosis and the symptom as so-called an autonomic imbalance (for example, hot flashes, sweating, malaise, and dizziness) appear.

Prolactin is a hormone secreted mainly from an anterior pituitary gland, and has the functions of, for example, growth acceleration of a mammary gland, acceleration of the production and secretion of milk, a gonadal suppression effect, retention of a luteal function, proliferation of endometrium, the water-electrolyte regulatory effect, and an immunostimulatory effect. Due to the decrease of the estrogen, a prolactin concentration in females is said to decrease from around the menopause.

The antidiuretic hormone is a hormone secreted from a posterior pituitary gland and acts on renal tubules of a kidney to concentrate urine and retain water in the body. When the function of the kidney deteriorates due to the aging, the function of concentrating urine is reduced and a large amount of thin urine is released, making it difficult to retain water in the body; the antidiuretic hormone has a function to suppress such a situation. Elderly people have the lower secretion quantity of the antidiuretic hormone, resulting in increased frequent urination, a urinary leakage, and night urination.

The parathyroid hormone is a hormone secreted from a parathyroid gland and has the function of keeping a calcium concentration in the blood and a body fluid together with calcitonin secreted from the thyroid gland and vitamin D. It is said that, with the aging, decreased calcium absorption leads to the continuous excessive secretion of the parathyroid hormone, and this excessive secretion leads to increased bone absorption and bone turnover, where osteoclast destroy old bones; causing the osteoporosis that is one of the geriatric diseases.

Melatonin is a hormone secreted by a pineal gland of the brain, and is also referred to as "sleeping hormone." Melatonin is involved in a biological rhythm of a living being, affects human sleeping and awakening, has the effect of calming nerves and causing the living being to direct to sleep at night. The secretion is high at night and a diurnal variation where the secretion stops on waking is observed. Melatonin is secreted most in a childhood, the secretion quantity of melatonin decreases with age, and the increase of melatonin at night becomes almost negligible after the age of 60 or older. Decrease of melatonin secretion quantity with the aging causes reduced sleep time, resulting in a sleep disorder; the elderly people often have the sleep disorder. Because melatonin promotes the metabolism of the cells and relieves the fatigue by an antioxidant effect, in addition to inducing the sleep, melatonin is said to exert an anti-aging effect, and is one of the hormones that are receiving attention. Furthermore, melatonin acts on the functions of various physiological active substances such as a neurotransmitter, the hormones, and a cytokine, and exerts its function as a biological response modifier that controls the nervous system and the immune system to adjust many biological functions, and this adjustment works in the direction of the anti-aging.

The anti-aging agent according to the present invention reduces the active oxygen (superoxide, hydrogen peroxide, hydroxyl radical), which is said to be one of the causes of the aging, to protect the cells from the active oxygen, thus contributing to the anti-aging. Consequently, for the purpose of reducing the active oxygen, the anti-aging agent according to the present invention can be used. In the living body, in particular, the active oxygen is easily generated in the skin when the skin is exposed to ultraviolet rays. Therefore, it is conceivable that the reduction of the active oxygen is one of the reasons of exerting the anti-aging effect in the skin as described above. While, in the anti-aging agent according to the present invention, the mechanism by which the active oxygen is reduced is under study, it is conceivable that the anti-aging agent exerts its effect by activating, for example, Sirt1 to enhance an antioxidant function inside the cells.

The method for manufacturing the anti-aging agent is not specifically limited, and a common manufacturing method used for manufacturing it may be appropriately chosen corresponding to its form. For example, when the form is powder, the anti-aging agent can be manufactured by uniformly mixing the nicotinamide mononucleotide and the other ingredient contained as necessary. The nicotinamide mononucleotide as the active ingredient is distributed in the market and commercially available. In particular, for the nicotinamide mononucleotide, a quality management system and a mass production system of the nicotinamide mononucleotide have recently been established.

The anti-aging agent according to the present invention is usable as a food product and a medicinal product. In the case of the use as the food product, the anti-aging agent can be provided as the food product for anti-aging in the food field. Daily ingestion in the form of the food product continuously provides the anti-aging effect, thus being especially effective in anti-aging. The type of the food product as the target of the present invention is not specifically limited, and the target includes a functional food, a food for specified health use, a dietary supplement, a food additive, a feed, a care food, a diet therapy food, a therapeutic diet, a diet food, and similar food product in addition to general food products. Specifically, for example, confectionery (gum, candies, cookies, gummi candies, biscuits, cakes, chocolates, Japanese confectionery, jelly, and the like), bread, noodles, rice/grain processed foods (cereals and the like), meat processed foods, fish and shellfish processed foods, vegetable processed foods, ready-prepared foods, fermented foods, seasonings (source, dressing, ketchup, and the like), spices, dairy products (yogurt, cheese, milk, and the like), ice cream, frozen foods, retort pouch foods, beverages (carbonated beverages, soft drinks, milk-based beverages, alcoholic beverages, sports beverages, fruit-flavored beverages, teas, nutritious beverages, concentrated beverages, and the like), powdered beverages (powdered juice, powdered soup, and the like) are exemplified. The form of the food product is not limited, and especially in the case of the functional food, the food for specified health use, and the like, the food product can be processed to be provided in the form of, for example, a powder, a tablet, a pill, a granule, a hard capsule formulation, a soft capsule formulation, a jelly, a liquid medicine, and a paste medicine.

The intake of the food product is different depending on the type of the food product, age, sex, and weight of a target that takes the food product, the expected effect, and the symptom. However, the daily intake per adult of the nicotinamide mononucleotide contained in the food product is ordinarily 1 mg to 500 mg, preferably 5 mg to 300 mg, and more preferably 50 mg to 300 mg. Less than 1 mg possibly fails to provide the effect of the present invention, while more than 500 mg merely provides almost similar effect but causes economic disadvantage. The compounding ratio of the nicotinamide mononucleotide in the food product can be appropriately set relative to a total food weight in a range of 100% or less.

The food product is safe and side effects are not specifically recognized. Therefore, the food product can be ingested over a long period of time for the purpose of the anti-aging. The food product can be applied to not only the elderly people but also the young people.

Meanwhile, the anti-aging agent according to the present invention can be administered orally or non-orally as a medicinal product (including quasi-drugs) for anti-aging in the pharmaceutical field. A dosage form of the medicinal product is not specifically limited, but can include, for example, a powder, a tablet, a persistent tablet, a chewable tablet, an effervescent tablet, a troche, a buccal tablet, a sublingual tablet, a capsule formulation, a fine granule, a granule, a pill, a dry syrup, a liquid medicine, a suspending agent, a syrup, a formulation for oral administration such as an elixir, and an eye drop, an eyewash, an eye ointment, an injection preparation, a transfusion, and an external preparation. Among these forms, considering the ease of taking, the stability of the active ingredient, and the like, the formulation for oral administration such as the powder, the tablet, and the capsule formulation is preferable.

The medicinal product can appropriately contain a known additive for formulation, which is adequate for the dosage form and pharmacologically allowed, considering physicochemical property, biological property, and similar property. Such an additive for formulation is exemplified by, for example, an excipient (lactose, starch, crystalline cellulose, sodium phosphate, and the like), a solvent (water, soybean oil, saline solution, a nonaqueous solvent for injection, and the like), a binder (starch, gelatin, gum arabic, sodium alginate, carmellose sodium, methylcellulose, ethyl cellulose, hydroxypropyl methylcellulose, hydroxypropyl cellulose, polyvinylpyrrolidone, and the like), a disintegrant (starch, carmellose sodium, and the like), a lubricant (talc, magnesium stearate, calcium stearate, macrogol, sucrose fatty acid ester, and the like), a coating agent (white sugar, HPC, shellac, gelatin, glycerin, hydroxypropyl methylcellulose, hydroxypropyl methylcellulose phthalate, cellulose acetate phthalate, and the like), a stabilizer (sodium bisulfite, sodium thiosulfate, sodium edetate, sodium citrate, ascorbic acid, dibutylhydroxytoluene, and the like), a preservative (methyl parahydroxybenzoate, ethyl parahydroxybenzoate, propyl parahydroxybenzoate, benzyl alcohol, phenol, chlorobutanol, benzalkonium chloride, benzethonium chloride, sodium dehydroacetate, thimerosal, and the like), a viscous agent (methylcellulose, carmellose sodium, chondroitin sulfate, sodium alginate, and the like), a suspending agent (various nonionic surfactant, methylcellulose, carmellose sodium, and the like), an emulsifier (gum arabic, cholesterol, sorbitan sesquioleate, polysorbate 80, sodium lauryl sulfate, and the like), a buffer (citric acid, acetic acid, sodium phosphate, and boric acid), a surfactant (hydrogenated castor oil, polysorbate 80, and the like), a colorant (water-soluble food pigment, lake pigment, and the like), a corrigent (lactose, white sugar, glucose, mannitol, and the like), a scenting agent (aromatic essential oils), a plasticizer (the phthalic acid esters, vegetable oils, polyethylene glycol, and the like).

A dose of the medicinal product cannot be equally specified because it differs depending on, for example, age, weight, and symptom of the administration target and the number of times of the administration. However, as the dose of the medicinal product, the daily amount per adult of the nicotinamide mononucleotide to be administered is ordinarily 1 mg to 500 mg, preferably 5 mg to 300 mg, and more preferably 50 mg to 300 mg. Less than 1 mg possibly fails to provide the effect of the present invention, while more than 500 mg merely provides almost similar effect but causes economic disadvantage. The compounding ratio of the nicotinamide mononucleotide in the medicinal product can be appropriately set in accordance with the dosage form, the dose of the medicinal product, and the like.

The number of times of the administration of the medicinal product can be appropriately set in accordance with, for example, the age, weight, and symptom of the administration target and the dose per administration of the medicinal product. The number of times of the medicinal product administration per day can be exemplified by once to three times.

Since the nicotinamide mononucleotide has the anti-aging effect as described above, the present invention further provides a method for anti-aging to cause a target that needs an effective dose of the nicotinamide mononucleotide to ingest it. That is, a method for anti-aging of the target of the ingestion by causing the target to ingest the anti-aging agent according to the present invention. The target of the ingestion is preferably a mammal such as a human, a mouse, a rat, a rabbit, a dog, a cat, cattle, a horse, a pig, and a monkey, and especially a human is preferable. In the method, the intake of the nicotinamide mononucleotide, the number of intake per day, and similar matters are as described for the anti-aging agent. The anti-aging agent can be ingested anytime in any case, and can be ingested by the target over a long period of time.

[Working Example]

The following describes the present invention in detail based on the working examples, while the present invention is not limited by these working examples.

[Working Example]
1. Evaluation of Melatonin Secretion Promoting Effect by Nicotinamide Mononucleotide In order to confirm a change in the melatonin quantity before and after ingestion of the nicotinamide mononucleotide, a test was conducted on healthy males and females aged 50 to 70 years.

As a sample of Working Example 1, a capsule formulation containing the nicotinamide mononucleotide and starch (100 mg (low dose) and 200 mg (high dose) of the nicotinamide mononucleotide in 4 capsules) (manufactured by SHINKOWA PHARMACEUTICAL Co., Ltd.) was used.

Each group consisting of five healthy males and females aged 50 to 70 years in an unbiased age group ingested the above low dose capsule formulation once a day by 4 capsules for 24 weeks (total 10 subjects, a low dose group: 100 mg/daily ingestion). On the other hand, each group consisting of five healthy males and females aged 50 to 70 years in the unbiased age group ingested the above high dose capsule formulation once a day by 4 capsules for 24 weeks (total 10 subjects, a high dose group: 200 mg/daily ingestion). In order to conduct appropriate evaluations, those who had been regularly using medical products for chronic diseases, those who had been consuming healthy foods that may affect clinical research, and those who were currently participating in other clinical researches or clinical trials, or had participated in other clinical researches or clinical trials within the last three months were excluded from the subject for the evaluation. The capsule formulations were ingested at 10 am (between meals and fasting state) together with water or lukewarm water (oral administration).

Figure 2A:
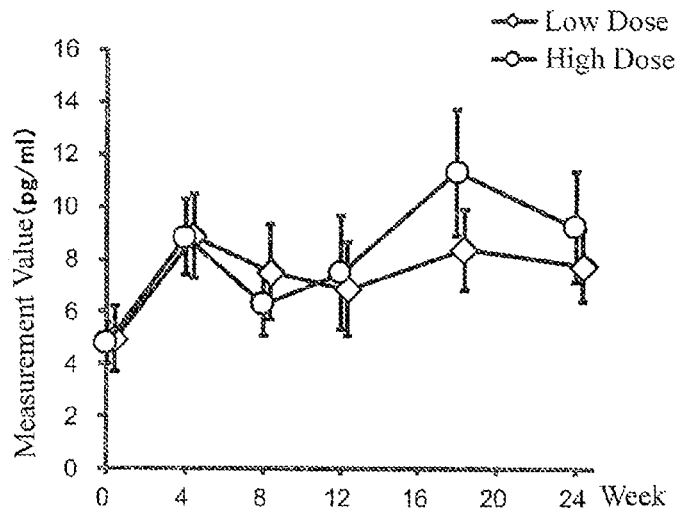
FIG. 2a is a drawing illustrating a transition of blood melatonin concentrations of the whole subjects when the nicotinamide mononucleotide was orally administered to the subjects for 24 weeks.
Figure 2B:
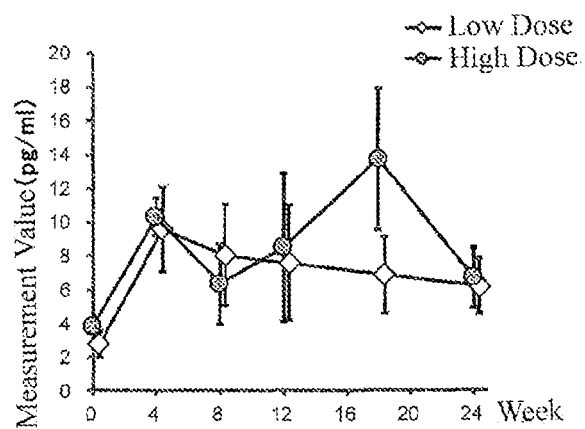
FIG. 2b is a drawing illustrating a transition of the blood melatonin concentrations of the male subjects when the nicotinamide mononucleotide was orally administered to the subjects for 24 weeks.
Figure 2C:
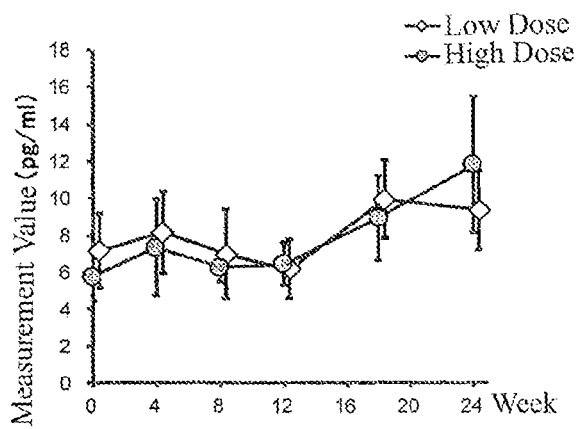
FIG. 2c is a drawing illustrating a transition of the blood melatonin concentrations of the female subjects when the nicotinamide mononucleotide was orally administered to the subjects for 24 weeks.
Figure 3A:
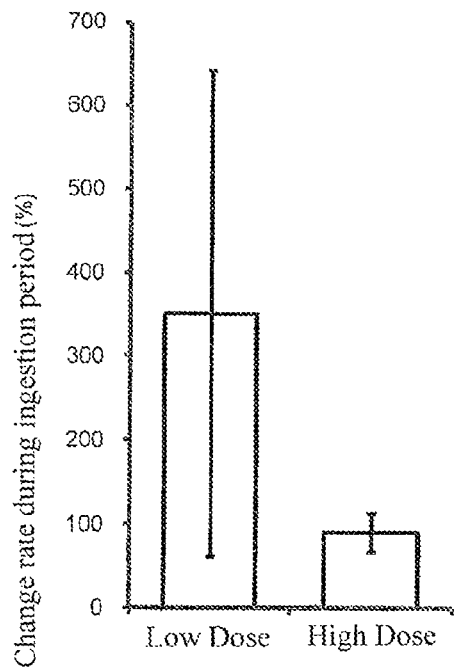
FIG. 3a is a drawing illustrating a change rate (%) of the blood melatonin concentrations of the whole subjects up to 24 weeks when the nicotinamide mononucleotide was orally administered to the subjects for 24 weeks.
Figure 3B:
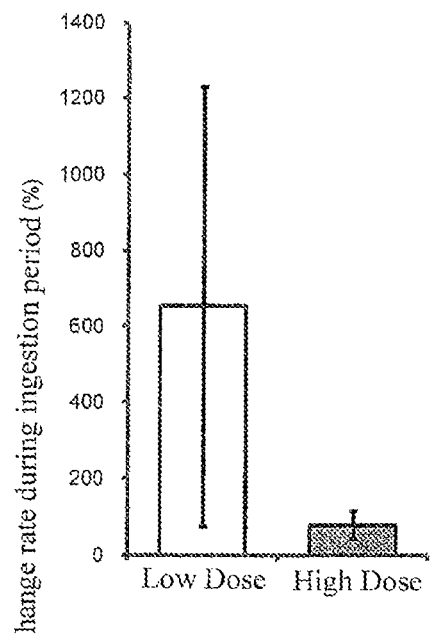
FIG. 3b is a drawing illustrating a change rate (%) of the male subjects up to 24 weeks when the nicotinamide mononucleotide was orally administered to the subjects for 24 weeks.
Figure 3C:
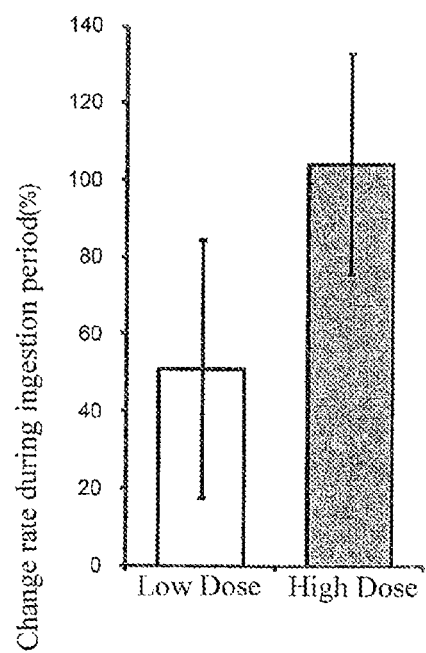
FIG. 3c is a drawing illustrating a change rate (%) of the female subjects up to 24 weeks when the nicotinamide mononucleotide was orally administered to the subjects for 24 weeks.

Measurement of the melatonin quantity in plasma was conducted by requesting the measurement to an external public organization according to a usual method. FIGS. 2a to 2c indicates transitions of the melatonin concentration (pg/ml) in the plasma for 24 weeks. FIG. 2a represents the transitions of the whole subjects; FIG. 2b represents the transitions of the male subjects; FIG. 2c represents the transitions of the female subjects. FIGS. 3a to 3c indicates change rates (%) of the blood melatonin concentration up to 24 weeks when the nicotinamide mononucleotide was orally administered to the subjects for 24 weeks. FIG. 3a represents the change rates of the whole subjects; FIG. 3b represents the change rates of the male subjects; FIG. 3c represents the change rates of the female subjects. Further, Table 1 indicates the numerical values of the melatonin concentration (pg/ml) in the plasma before the ingestion of the nicotinamide mononucleotide (0 weeks) and after the ingestion of the nicotinamide mononucleotide (24 weeks). In addition, the numerical values represent mean values±standard deviation.

TABLE 1

| | Group | 0 weeks (before ingestion) | 24 weeks (after ingestion) | Change rate (24 weeks- 0 weeks) |
|---|---|---|---|---|
| Whole Subjects | High Dose Group | 4.80 ± 2.44 | 92.4 ± 6.65 | 4.45 ± 4.75 |
| | Low Dose Group | 4.96 ± 3.96 | 7.78 ± 4.36 | 2.82 ± 3.26 |
| Male | High Dose Group | 3.82 ± 1.41 | 6.68 ± 4.04 | 2.86 ± 3.10 |
| | Low Dose Group | 2.76 ± 1.71 | 6.20 ± 3.60 | 3.44 ± 3.57 |
| Female | High Dose Group | 5.77 ± 3.00 | 11.81 ± 8.17 | 6.03 ± 5.90 |
| | Low Dose Group | 7.15 ± 4.51 | 9.37 ± 4.85 | 2.21 ± 3.19 |

2. Evaluation Results

As can be seen from the results shown in FIGS. 2a to 2c and FIGS. 3a to 3c, the ingestion of the nicotinamide mononucleotide increased the melatonin concentrations in plasma at the high change rates. In addition, as shown in Table 1, as a whole, a significant difference was observed in both the low dose group and the high dose group compared to the melatonin concentrations in the plasma before ingestion ($p<0.05$).

From the above results, the melatonin secretion promoting effect by orally administering the nicotinamide mononucleotide to the middle-aged males and females was confirmed, and it was clarified that the nicotinamide mononucleotide is effective in the anti-aging.

In addition, the subjects of the above evaluation did not show any unidentified complaint such as an abdominal pain, nausea, vomiting, or a headache or a stool abnormality even after the ingestion for 24 weeks, and this ensured the safety of the nicotinamide mononucleotide.

The invention claimed is:

1. A method for increasing melatonin level in a subject over 50 years of age, comprising administrating by ingestion to the subject in need thereof an effective dose of a nicotinamide mononucleotide, wherein the effective dose is obtained by maintaining the increase of melatonin after administration.

2. The method according to claim 1, wherein the nicotinamide mononucleotide is administered as a food product.

3. The method according to claim 1, wherein the nicotinamide mononucleotide as an anti-aging agent is administered as a medical product.

* * * * *